United States Patent [19]

Matsumoto et al.

[11] Patent Number: 4,705,884
[45] Date of Patent: Nov. 10, 1987

[54] FLUORINE-SUBSTITUTED PHENYL BENZOATES AND PROCESS FOR PRODUCING SAME

[75] Inventors: Masakatsu Matsumoto, Sagamihara; Yasunobu Nishimura, Kamifukuoka, both of Japan

[73] Assignees: Sagami Chemical Research Center, Tokyo; Central Glass Company, Limited, Yamaguchi, both of Japan

[21] Appl. No.: 878,862

[22] PCT Filed: Oct. 8, 1985

[86] PCT No.: PCT/JP85/00556
§ 371 Date: Jun. 5, 1986
§ 102(e) Date: Jun. 5, 1986

[87] PCT Pub. No.: WO86/02067
PCT Pub. Date: Apr. 10, 1986

[30] Foreign Application Priority Data
Oct. 8, 1984 [JP] Japan .................... 59-209895

[51] Int. Cl.⁴ .............................. C07C 69/76
[52] U.S. Cl. .................................... 560/109
[58] Field of Search ........................... 560/109

[56] References Cited
FOREIGN PATENT DOCUMENTS

| | | | |
|---|---|---|---|
| 49-92228 | 9/1974 | Japan | 560/109 |
| 54-39039 | 3/1979 | Japan | 560/109 |
| 58-213728 | 12/1983 | Japan | 560/109 |

*Primary Examiner*—Paul J. Killos
*Attorney, Agent, or Firm*—Wenderoth, Lind & Ponack

[57] ABSTRACT

A fluorine-substituted phenyl benzoate of the general formula $$Ar-CO_2-Ar' \qquad (I)$$

wherein one of either Ar or Ar' is p- or o-fluorophenyl group, while the other is m-fluorophenyl group.

This fluorine-substituted phenyl benzoate can be prepared by subjecting to an oxidative decarboxylation reaction a fluorobenzoic acid of the general formula $$Ar''-CO_2H \qquad (II)$$

wherein Ar'' is a fluorophenyl group. This phenyl benzoate is valuable as in intermediate for producing the fluorophenols.

5 Claims, No Drawings

FLUORINE-SUBSTITUTED PHENYL BENZOATES AND PROCESS FOR PRODUCING SAME

FIELD OF TECHNOLOGY

This invention relates to new substituted benzoic acid derivatives. More specifically, the invention relates to fluorine-substituted phenyl benzoates having the general formula $$Ar-CO_2-Ar' \qquad (I)$$

wherein one of either Ar or Ar' is p- or o-fluorophenyl group, while the other is m-fluorophenyl group, as well as a process for producing these phenyl benzoates.

The fluorine-substituted phenyl benzoates of the general formula (I) can be used as a starting material for producing the fluorophenols, which are valuable as intermediates for synthesizing medicines, agricultural drugs or functional materials. Specifically, the fluorophenols can be easily derived from the compounds of general formula (I) by hydrolysis.

PRIOR ART

Known heretofore as processes for producing the fluorophenols are say (a) that of subjecting fluoroaniline to the Sandmeyer reaction [Ger. Offen No. 2,426,994 (1975)]; (b) that of subjecting aminophenol to the Schiemann reaction [Dunker, M. F. W.; Starkey, E. B., *J. Am. Chem. Soc.*, 1939, 11, 3005 and Finger, G. C.; Oesterling, R. E., *J. Am. Chem. Soc.*, 1956, 78, 2593]; (c) that of hydrolyzing bromofluorobenzene [Boudakian, M. M.; Eber, R. J.; McArthur, R. E., *J. Org. Chem.*, 1961, 26, 4641]; and (d) that of subjecting fluoroanisole to acid decomposition [Suter, C. M.; Lawson, E. J.; Smith, P. G., *J. Am. Chem. Soc.*, 1939, 61, 165]. These conventional processes have however the following defects. In the case of the process of (a) not only is there the problem of procuring the starting material, but also a large amount of an acid such as sulfuric acid must be used. The process of (b) requires the use of borofluoric acid of high purity, which cannot be reused. Not only are the reaction conditions harsh in the case of process of (c), but also there is the possibility of a defluorination reaction taking place concurrently, as well as a tendency to the formation as a by-product of unsubstituted phenol, whose separation from the fluorophenols is difficult. On the other hand, in the case of the process of (d), the starting materials other than p-fluoroanisole are not readily available, and hence the process is restricted to the synthesis of only the p-isomer of the fluorophenols.

The conventional processes thus had their shortcomings in that the fluorophenols could not be produced by a simple and convenient process or that it was not possible to produce the fluorophenol isomers, as desired. They were thus not employable on an industrial scale.

DISCLOSURE OF THE INVENTION

Extensive investigations were made by the present inventors for an industrially feasible process for producing the fluorophenols. These investigations led to the discovery of the fluorine-substituted phenyl benzoates of general formula (I), a precursor of the fluorophenols, and to the perfection of an industrially advantageous process for its production.

The fluorine-substituted phenyl benzoates of general formula (I) provided by the present invention can be easily produced by subjecting to an oxidative decarboxylation reaction a fluorobenzoic acid of the general formula $$Ar''-CO_2 \qquad (II)$$

wherein Ar'' is a fluorophenyl group.

Fluorobenzoic acid of general formula (II) used in the above reaction is a compound known per se. For example, it is a compound that can be obtained easily at low cost by the oxidation of fluorotoluene.

The oxidative decarboxylation reaction of the fluorobenzoic acid of general formula (II) can usually be carried out by bringing the fluorobenzoic acid into contact with an oxidizing agent in a solventless state or preferably in an inert organic solvent having a relative high boiling point (preferably ranging from 180° to 260° C.) and capable of being refluxed at the reaction temperature, such as diethyl fumarate, diphenyl ether, tetraglyme and decalin. Usable in this case as the oxidizing agent are, for example, the cupric salts and such combinations as oxygen and a catalytic amount of copper, cuprous or cupric salt, or copper oxide. Examples of usable copper or copper salts include copper powder and porous copper; cuprous halide and cupric halide; organic acid salts of copper such as copper fluorobenzoate and copper acetate; basic copper carbonate and copper hydroxide. When a cupric salt such as cupric hydroxide is used alone as the oxidizing agent, the cupric salt is conveniently used in about an equimolar quantity to the fluorobenzoic acid of general formula (II), preferably in an amount of 0.5 to 2 moles per mole of the latter. An assistant catalyst such as magnesium oxide, zirconium oxide or manganese dioxide may also be used, as required.

The reaction is usually carried out at a temperature above about 180° C., but from the standpoint of reaction efficiency such as the rate of reaction and prevention of side reactions, the reaction is suitably carried out at a temperature ranging from 200° to 260° C.

The compound of general formula (I) formed by the foregoing reaction can be separated from the reaction mixture and/or be purified by such already per se known means as chromatography, crystallization, recrystallization, distillation and extraction.

In the aforementioned oxidative decarboxylation reaction it is believed that the fluorobenzoic acid of general formula (II) reacts with the oxidizing agent and forms cupric fluorobenzoate as an intermediate, which then is converted to the fluorine-substituted phenyl benzoate of formula (I) under the foregoing temperature conditions. This is corroborated by the experiments shown in the hereinafter-given Referential Examples 1 and 2. It was confirmed in these referential examples that the fluorine-substituted phenyl benzoate of formula (I) is formed by exposing the cupric fluorobenzoate to the aforesaid temperature conditions.

Further, the fluorine-substituted phenyl benzoate of general formula (I) can be converted to fluorophenol by subjecting it to hydrolysis. And when it is desired to obtain fluorophenol, the preparation of the phenyl benzoate and its hydrolysis can be performed in a single pot. In this case, it is also possible, for example, as shown in the hereinafter-given Examples 6 and 7, to add the copper catalyst and optionally an assistant catalyst to the fluorobenzoic acid of general formula (II) followed by feeding oxygen and superheated steam to carry out the formation of the fluorine-substituted phenyl benzoate and its hydrolysis in a single step.

PREFERRED MODES OF CARRYING OUT THE INVENTION

The following working and referential examples will serve to more specifically illustrate the present invention.

EXAMPLE 1

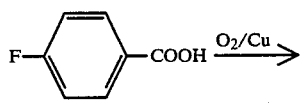

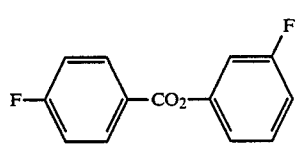

A 10-ml Claisen distillation flask fitted with an oxygen introducing line was charged with 1.4 g of p-fluorobenzoic acid, 0.159 g of powdered porous copper, and 0.3 g of diethyl fumarate as solvent, after which the flask was heated at 240° C. over an oil bath. Inthe meantime, oxygen was blown in from the bottom of the reaction mixture via the oxygen introducing line at a rate of 30 ml per minute over a period of 50 minutes. The unreacted oxygen and the carbon dioxide formed by the reaction were discharged externally of the Claisen flask via its branched line. After cooling, the reaction mixture was eluted using diethyl ether and separated by filtration into a filtration residue and filtrate. The filtration residue was washed with 6N hydrochloric acid to liberate p-fluorobenzoic acid, which was then dissolved in diethyl ether, followed by extraction, concentration and drying to recover 0.192 g of p-fluorobenzoic acid. The filtrate (diethyl ether layer) was washed twice with 6N hydrochloric acid and, after concentration, submitted to column chromatography (solid phase: silica gel, developing solvent: hexane→methylene chloride, ethyl acetate) to give 0.520 g of m-fluorophenyl p-fluorobenzoate, 0.011 g of m-fluorophenol and 0.518 g of p-fluorobenzoic acid. The yield of m-fluorophenyl p-fluorobenzoate was 44.0%, and the selectivity was 89.2%.

Properties of m-fluorophenyl p-fluorobenzoate

Colorless flaky crystals (on recrystallization from hexane).

Melting point: 43.5°–45.2° C. $^{19}$F-NMR (CDCl$_3$:CFCC$_3$): $\delta$ —105 (t of t, J=6 and 5Hz), —112 (m). MS m/z (%): 234 (M$^+$, 2), 75 (12), 95 (38), 123 (100). IR (KBr): 1735 cm$^{-1}$.

Elementary analysis for C$_{13}$H$_8$F$_2$O$_2$:

|  | C | H |
|---|---|---|
| Calcd. (%): | 66.67 | 3.44 |
| Found (%): | 66.80 | 3.34 |

EXAMPLE 2

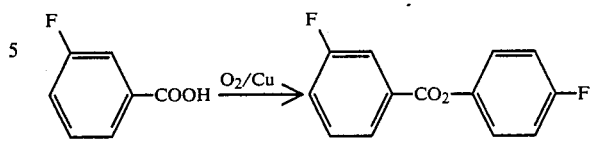

A 30-ml Claisen distillation flask fitted with an oxygen introducing line was charged with 4.9 g of m-fluorobenzoic acid, 0.223 g of powdered porous copper, and 0.5 g of diethyl fumarate as solvent, after which it was heated at 250° C. over an oil bath. In the meantime, oxygen was blown in from the bottom of the reaction mixture via the oxygen introducing line at a rate of 40 ml per minute for a period of 60 minutes. After cooling, 0.602 g of m-fluorobenzoic acid was recovered from the filtraton residue by operating as in Example 1. And from the filtrate there were obtained by column chromatography 0.406 g of p-fluorophenyl m-fluorobenzoate and 3.81 g of m-fluorobenzoic acid. The yield of p-fluorophenyl m-fluorobenzoate was 5.0%, and the selectivity was 50.2%.

Properties of p-fluorophenyl m-fluorobenzoate

Colorless flaky crystals (on recrystallization from hexane).

Melting point: 63.5°–66.0° C. $^{19}$F-NMR (CDCl$_3$:CFCl$_3$): $\delta$ —112 (d of d of d), —117 (t of t). MS m/z (%): 234 (M$^+$, 5), 75 (14), 95 (48), 123 (100). IR (KBr): 1730 cm$^{-1}$.

Elementary analysis for C$_{13}$H$_8$F$_2$O$_2$:

|  | C | H |
|---|---|---|
| Calcd. (%): | 66.67 | 3.44 |
| Found (%): | 66.82 | 3.38 |

EXAMPLE 3

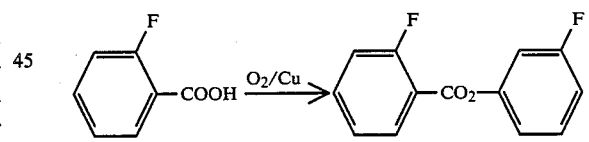

A 30-ml Claisen distillation flask fitted with an oxygen introducing line was charged with 4.9 g of o-fluorobenzoic acid, 0.223 g of powdered porous copper, and 0.5 g of diethyl fumarate as solvent, after which it was heated at 240° C. over an oil bath. In the meantime, oxygen was blown in from the bottom of the reaction mixture via the oxygen introducing line at a rate of 40 ml per minute over a period of 60 minutes. After cooling, 1.014 g of o-fluorobenzoic acid was recovered from the filtration residue by operating as in Example 1. And from the filtrate there were obtained by column chromatography 1.472 g of m-fluorophenyl o-fluorobenzoate and 1.154 g of o-fluorobenzoic acid. The yield of m-fluorophenyl o-fluorobenzoate was 36.0%, and the selectivity was 77.6%.

Properties of m-fluorophenyl o-fluorobenzoate

Colorless flaky crystals (on recrystallization from hexane).

Melting point: 37.5°–38.5° C. $^{19}$F-NMR (CDCl$_3$:CFCl$_3$): δ −108 (m), −111 (m). MS m/z (%): 234 (M+, 4), 75 (13), 95 (27), 123 (100). IR (KBr): 1742 cm$^{-1}$.

Elementary analysis for C$_{13}$H$_8$F$_2$O$_2$:

|  | C | H |
| --- | --- | --- |
| Calcd. (%): | 66.67 | 3.44 |
| Found (%): | 66.50 | 3.41 |

EXAMPLE 4

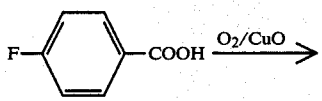

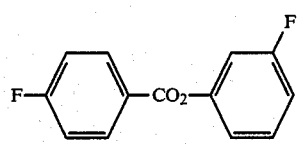

A 25-ml 2-necked Kjeldahl flask fitted with an air-cooling line and an oxygen introducing line was charged with 2.1 g of p-fluorobenzoic acid, 1.99 g of cupric oxide, and 2 ml of diphenyl ether as solvent, after which it was heated at 240° C. over an oil bath while blowing in oxygen at a rate of 30 ml per minute for 90 minutes. After cooling, the experiment was carried out as in Example 1 to recover 0.121 g of p-fluorobenzoic acid from the filtration residue. And from the filtrate there were obtained 0.656 g of m-fluorophenyl p-flurobenzoate and 1.000 g of p-fluorobenzoic acid by column chromatography. The yield of m-fluorophenyl p-fluorobenzoate was 37.4%, and the selectivity was 80.3%.

EXAMPLE 5

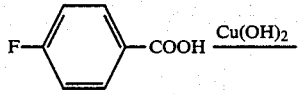

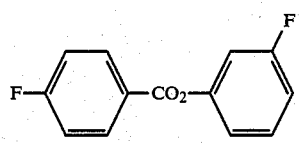

A 25-ml Kjeldahl flask fitted with an air-cooling line was charged with 1.4 g of p-flurobenzoic acid, 0.976 g of cupric hydroxide, and 3 ml of tetraglyme as solvent, after which it was heated at 240° C. over an oil bath. This temperature was maintained for 60 minutes. After cooling, the reaction mixture was eluted with diethyl ether followed by filtration using Celite. the resulting filtrate was then submitted to column chromatography (solid phase: silica gel, developing solvent: hexane→methylene chloride) to give 0.013 g of m-fluorophenyl p-fluorobenzoate.

REFERENTIAL EXAMPLE 1

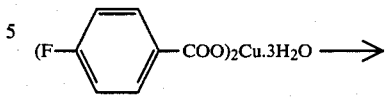

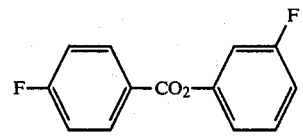

A screwed cap-fitted glass sample tube having a diameter of 20 mm and a height of 150 mm was charged with 2.966 g of cupric p-fluorobenzoate trihydrate and 6 ml of decalin as solvent. The tube was then heated at 150° C. for about 15 minutes, after which it was capped and maintained at 240° C. for 90 minutes. After cooling, the tube was opened, and the reaction mixture was eluted with methylene chloride and filtered using Celite. The resulting filtrate was then concentrated and submitted to column chromatography (solid phase: silica gel, developing solvent: hexane→methylene chloride) to give 0.243 g of m-fluorophenyl p-fluorobenzoate at a yield of 13.8%.

REFERENTIAL EXAMPLE 2

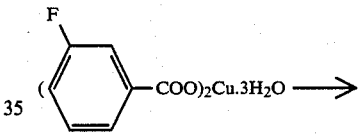

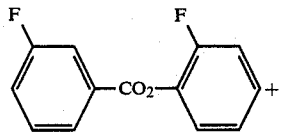

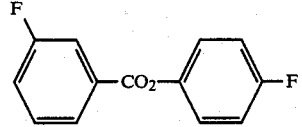

A screwed cap-fitted glass sample tube having a diameter of 20 mm and a height of 150 mm was charged with 1.978 g of cupric m-fluorobenzoate trihydrate and 4 ml of decalin as solvent. The tube was then heated at 150° C. for about 15 minutes, after which it was capped and held at 230° C. for 90 minutes. After cooling, the tube was opened, and the reaction mixture was eluted with methylene chloride and filtered using Celite. The resulting filtrate was then concentrated and submitted to column chromatography (solid phase: silica gel, developing solvent: hexane→methylene chloride) to give 0.251 g of a mixture of o-fluorophenyl m-fluorobenzoate and p-fluorophenyl m-fluorobenzoate. The proportion in which the o-fluorophenyl m-fluorobenzoate and the p-fluorophenyl m-fluorobenzoate were formed was found to be about 1:9 from the $^{19}$F-NMR integral ratio. On recrystallization of this mixture from hexane, the p-fluorophenyl m-fluorobenzoate was obtained in pure form.

The o-fluorophenyl m-fluorobenzoate was identified by comparison of its spectral data with those of an authentic sample synthesized from m-fluorobenzoic acid and o-flurophenol.

Properties of o-fluorophenyl m-fluorobenzoate

Colorless flaky crystals (on recrystallization from hexane).

Melting point: 30.7°–31.8° C. $^{19}$F-NMR (CDCl$_3$:CFCl$_3$): δ−123 (m), −129 (m). MS m/z (%): 234 (M$^+$, 5), 75 (11), 95 (40), 123 (100).

IR (KBr): 1745 cm$^{-1}$.

Elementary analysis for C$_{13}$H$_8$F$_2$O$_2$:

|  | C | H |
| --- | --- | --- |
| Calcd. (%): | 66.67 | 3.44 |
| Found (%): | 66.43 | 3.43 |

REFERENTIAL EXAMPLE 3

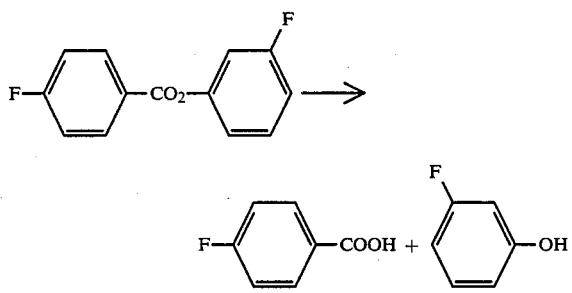

Sodium hydroxide (0.118 g) was dissolved in 2 ml of methanol in a 10-ml Kjeldahl flask, after which 0.234 g of m-fluorophenyl p-fluorobenzoate was added. The mixture was then heated under reflux for 60 minutes. After cooling, the reaction mixture was neutralized with 0.25 ml of concentrated hydrochloric acid. The precipitated p-fluorobenzoic acid was completely dissolved by the addition of about 5 ml of diethyl ether. This was followed by the addition of a small amount of magnesium sulfate, removal of water and filtration. The resulting filtrate was then distilled under reduced pressure to give 0.070 g of m-fluorophenol at a yield of 63%. The distillation residue, after being dissolved in diethyl ether, was removed and concentrated, following which it was submitted to column chromatography (solid phase: silica gel, developing solvent: methylene chloride) to give 0.139 g of p-fluorobenzoic acid at a yield of 99.3%.

REFERENTIAL EXAMPLE 4

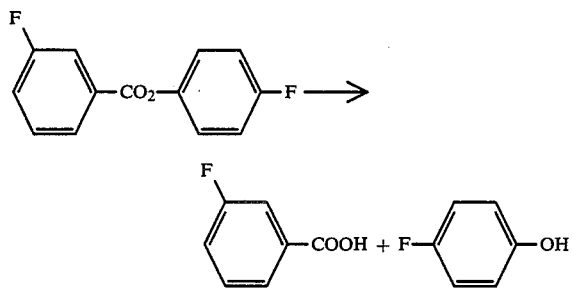

A 10-ml Kjeldahl flask equipped with a reflux condenser was charged with a solution of 0.118 g of sodium hydroxide in 2 ml of methanol followed by the addition of 0.234 g of p-fluorophenyl m-fluorobenzoate, after which the mixture was heated under reflux for 60 minutes. After cooling, the reaction mixture was neutralized with 0.25 ml of concentrated hydrochloric acid. The precipitated m-fluorobenzoic acid was completely dissolved by the addition of about 8 ml of diethyl ether, and 0.1 g of hexamethylbenzene was then added as an internal standard substance for gas chromatography. Next, a small amount of magnesium sulfate was added and, after removal of water, quantitative analysis was performed by means of gas chromatography (filler: Silicone SE-30, 1 m, carrier gas: He, 130°→180° C., 5° C./min. rise in temperature, TCD). It was confirmed that 140 mg (yield 100%) of m-fluorobenzoic acid and 108 mg yield 96%) of p-fluorophenol were contained.

REFERENTIAL EXAMPLE 5

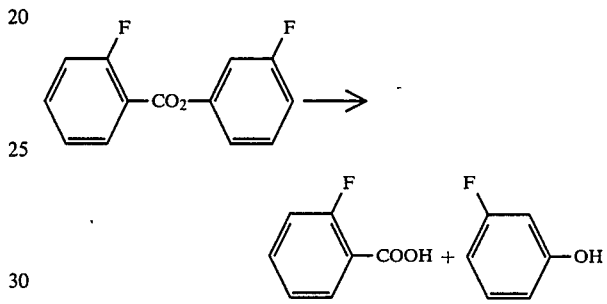

Sodium hydroxide (0.109 g) was dissolved in 2 ml of methanol in a 10-ml Kjeldahl flask fitted with a reflux condenser, after which 0.234 g of m-fluorophenyl o-fluorobenzoate was added, and the mixture was heated under reflux for 60 minutes. After cooling, the experiment was operated as in Referential Example 4 to confirm that the reaction mixture contained 140 mg (yield 100%) of o-fluorobenzoic acid and 112 mg (yield 100%) of m-fluorophenol.

EXAMPLE 6

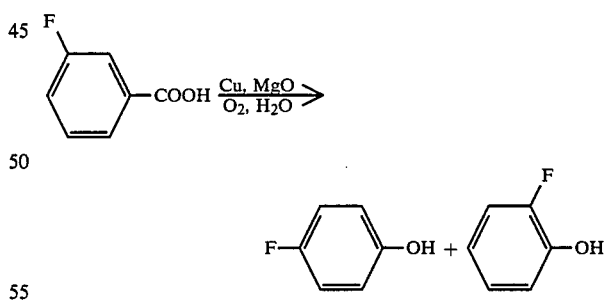

A tubular reactor of glass having a diameter of 25 mm and a height of 350 mm and fitted with a branched distillation line and at its bottom a gas introducing line was charged with 14 g of m-fluorobenzoic acid, 0.218 g of powdered porous copper and 0.200 g of magnesium oxide. While heating the mixture at 238° C., a gaseous mixture of oxygen [15 ml (volume under the conditions of room temperature and 1 atm) per minute ] and superheated steam (H$_2$O 0.10 g per minute) was blown in for 3 hours and 30 minutes.

The p- and o-fluorophenols formed by the reaction were subjected to steam distillation, passed via the branched distillation line and cooled to be collected as distillates. On the other hand, the unreacted oxygen and carbon dioxide formed by the reaction were passed via the branched distillation line and discharged externally of the system. After termination of the reaction, the organic matter contained in the distillates was extracted with diethyl ether, and it was confirmed by 19$^F$-NMR that the p- and o-fluorophenols were contained in a ratio of 6:1. This ethereal solution was concentrated and distilled under reduced pressure to give 1.936 g of a mixture of p- and o-fluorophenols. On the other hand, the distillation residue was quantitatively analyzed by gas chromatography (filler: Silicone SE-30, 1 m, carrier gas: He, 130°→180° C., 5° C./min. rise in temperature, TCD) to confirm the content of 0.326 g of a mixture of p- and o-fluorophenols, 1.569 g of m-fluorobenzoic acid and 0.015 g of p-fluorohenyl m-fluorobenzoate.

The residue in the reactor was eluted with diethyl ether, following which it was washed with 6N hydrochloric acid and then filtered to remove the diethyl ether-insoluble portion (tar). Next, the ether layer was washed with an aqueoud 2N sodium hydroxide solution and then separated into an ether layer and an aqueous layer. From the ether layer was obtained 0.354 g of p-fluorophenyl m-fluorobenzoate by drying and concentrating the ether layer. The aqueous layer, after neutralization, was acidified, and the precipitated white solid was dissolved in diethyl ether, extracted, dried and concentrated to give 8.684 g of m-fluorobenzoic acid.

The yield of p- and o-fluorophenols was 20.2%, and the selectivity was 85.6%. The foregoing selectivity was calculated by the following equation.

$$\text{Selectivity (\%)} + \frac{B}{A - A' - 2C} \times 100$$

where
A is the number of moles of m-fluorobenzoic acid used,
A' is the number of moles of m-fluorobenzoic acid recovered,
B is the number of moles of p- and o-fluorophenols, and
C is the number of moles of p-fluorophenyl m-fluorobenzoate.

EXAMPLE 7

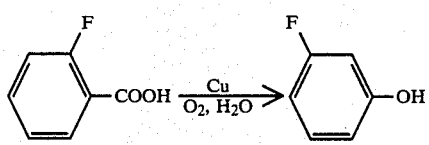

A reactor of glass having a diameter of 25 mm and a height of 350 mm and fitted with a branched distillation line, a gas introducing line at its bottom, and a thermometer was charged with 14 g of o-fluorobenzoic acid and 0.159 g of powdered porous copper and heated at 240° C. A gaseous mixture of oxygen [18 ml (volume under the conditions of room temperature and 1 atm)/min.] and superheated steam (H$_2$O 0.10 g/min.) was then blown for 3 hours via the gas introducing line.

The m-fluorophenol formed by the reaction was subjected to steam distillation, passed via the branched distillation line and cooled to be collected as a distillate. On the other hand, the unreacted oxygen and the carbon dioxide formed by the reaction were passed via the branched distillation line and discharged externally of the system.

After termination of the blowing in of the gaseous mixture, the inside temperature was lowered to 120° C. while blowing in argon and 10 ml of water was added to drive out the residual m-fluorophenol along with water. The organic matter in the distillate was extracted with diethyl ether, and 1.602 g of m-fluorophenol (b.p. 80° C./20 mmHg) was obtained by distillation under reduced pressure. Further, when quantitative analysis of the distillation residue was performed by submitting it to gas chromatography (filler: Silicone SE-30, 1 m, carrier gas: He, 130°→180° C., 5° C./min. rise in temperature, TCD), the content of 0.025 g of m-fluorophenol, 1.004 g of o-fluorobenzoic acid and 0.025 g of m-fluorophenyl o-fluorobenzoate was confirmed.

The residue in the reactor was eluted with diethyl ether, washed with 6N hydrochloric acid and filtered to remove the ether-insoluble portion (tar). Next, the ether layer was washed with an aqueous 2N sodium hydroxide solution, after which the ether layer and the aqueous layer were separated. From the ether layer was obtained 0.660 g of m-fluorophenyl o-fluorobenzoate by drying and concentration. The aqueous layer, after neutralization, was acidified, and the precipitated white solid was dissolved in diethyl ether, extracted, dried and concentrated to give 9.653 g of o-fluorobenzoic acid.

The yield of m-fluorophenol was 14.5%, and the selectivity was 80.4%.

POSSIBILITY OF UTILIZATION IN INDUSTRY

The fluorine-substituted phenyl benzoates of the aforesaid general formula (I) provided by the present invention can be used as a starting material for producing the fluorophenols, which are valuable as intermediates for synthesizing medicines, agricultural chemicals of functional materials.

What is claimed is:

1. A fluorine-substituted phenyl benzoate having the general formula

wherein one of either Ar or Ar' is a member selected from the group consisting of the p- and o-fluorophenyl groups, and the other is m-fluorophenyl group.

2. A process for producing a fluorine-substituted phenyl benzoate of the general formula

wherein one of either Ar or Ar' is a member selected from the group consisting of the p- and o-fluorophenyl groups, and the other is m-fluorophenyl group, said process comprising subjecting to an oxidative decarboxylation reaction a fluorobenzoic acid of the general formula

wherein Ar'' is a fluorophenyl group.

3. The process of claim 2 wherein said oxidative decarboxylation reaction is carried out by bringing the fluorobenzoic acid of formula (II) into contact with an oxidizing agent.

4. The process of claim 3 wherein the oxidizing agent is a member selected from the group consisting of the cupric salts and the combinations of oxygen with a catalytic amount of a member of the group consisting of the copper, cuprous and cupric salt, and copper oxide.

5. The process of claim 3 wherein said contact is carried out at a temperature ranging from 200° to 260° C.

* * * * *